United States Patent [19]
Bethge et al.

[11] 4,416,827
[45] Nov. 22, 1983

[54] PROCESS FOR THE RESOLUTION OF THE RACEMATE (1RS,2SR)-2-AMINO-1-PHENYL-PROPAN-1-OL

[75] Inventors: Horst Bethge; Axel Kleemann, both of Hanau; Jürgen Martens, Alzenau, all of Fed. Rep. of Germany

[73] Assignee: Degussa Aktiengesellschaft, Frankfurt, Fed. Rep. of Germany

[21] Appl. No.: 411,325

[22] Filed: Aug. 25, 1982

[30] Foreign Application Priority Data

Aug. 28, 1981 [DE] Fed. Rep. of Germany ....... 3134129

[51] Int. Cl.$^3$ .................. C07C 99/12; C07C 85/26
[52] U.S. Cl. ............... 260/501.12; 562/401; 564/355
[58] Field of Search .............. 260/501.12; 562/401; 564/355

[56] References Cited

U.S. PATENT DOCUMENTS

| 3,595,302 | 5/1976 | Asinger | 562/554 |
| 3,808,268 | 4/1974 | Rambacher et al. | 562/401 |
| 4,224,457 | 9/1980 | Iwao et al. | 562/401 |

FOREIGN PATENT DOCUMENTS

| 2138121 | 2/1973 | Fed. Rep. of Germany | 562/554 |
| 2147812 | 4/1973 | France | 562/554 |

OTHER PUBLICATIONS

Nagai, Liebigs Ann. Chem., vol. 470, pp. 157–182 (1929).
Armstrong, J. Amer. Chem. vol. 16, pp. 749–753 (1971).

*Primary Examiner*—James H. Reamer
*Attorney, Agent, or Firm*—Cushman, Darby & Cushman

[57] ABSTRACT

There is described the resolution of the racemate (1RS,2SR)-2-amino-1-phenyl-propan-1-ol. It is carried out by means of the optical isomers of S-(carboxymethyl)-cysteine.

13 Claims, No Drawings

PROCESS FOR THE RESOLUTION OF THE RACEMATE (1RS,2SR)-2-AMINO-1-PHENYL-PROPAN-1-OL

BACKGROUND OF THE INVENTION

The invention is directed to a process for the resolution of the racemate (1RS,2SR)-2-amino-1-phenyl-propan-1-ol, especially for the purpose of recovery of (1R,2S)-2-amino-1-phenyl-propan-1-ol. This substance is an important starting material for the synthesis of medicines.

It is known to separate (1R,2S)-2-amino-1-phenyl-propan-1-ol, also called 1-norephedrine, from the racemate (1RS,2SR)-2-amino-1-phenyl-propan-1-ol by means of optically active tartaric acid (Nagai, Liebigs Ann. Chem. Vol. 470, pages 157-182 (1929)). This process is unsatisfactory because the diastereomer salts involved are only slightly different in their solubility.

Besides, it is known to resolve the racemate (1RS,2SR)-2-amino-1-phenyl-propan-1-ol by means of the optical isomers of 3-formyl-2,2,5,5-tetramethyl-thiazolidin-4-carboxylic acid (German patent 2138121 and related Asinger U.S. Pat. No. 3,959,302. The entire disclosure of Asinger is hereby incorporated by reference and relied upon). The diastereomeric salts involved have moderately good solubility differences, but a disadvantage of this process is that the thiazolidine-carboxylic acid has only slight stability.

SUMMARY OF THE INVENTION

It has now been found that the racemate (1RS,2SR)-2-amino-1-phenyl-propan-1-ol can be resolved by means of the optical isomers of S-(carboxymethyl)cysteine. The S-(carboxymethyl)-cysteine is very stable under the conditions of the process and the diastereomeric salts differ very greatly in their solubility. The optical isomers of 2-amino-1-phenyl-propan-1-ol are obtained in high yields in outstanding optical and chemical purity.

The optical isomers of S-(carboxymethyl)-cysteine can be produced from the optical isomers of cysteine, for example, by conversion by means of chloroacetic acid in alkaline medium according to the process set forth in Amstrong, J. Org. Chem. Vol. 16 (1951) pages 749 to 753.

According to the invention, the (1R,2S)-2-amino-1-phenyl-propan-1-ol is separated from the racemate by means of S-(carboxymethyl)-(R)-cysteine and the (1S,2R)-2-amino-1-phenyl-propan-1-ol by means of S-(carboxymethyl-(S)-cysteine. The salts formed from (1R,2S)-2-amino-1-phenyl-propan-1-ol and S-(carboxymethyl)-(R)-cysteine as well as from (1S,2R)-2-amino-1-phenyl-propan-1-ol and S-(carboxymethyl)-(S)-cysteine previously have not been described. The salt of (1R,2S)-2-amino-1-phenyl-propan-1-ol and S-(carboxymethyl)-(R)-cysteine is considerably less soluble than the diastereomer salt thereto from (1S,2R)-2-amino-1-phenyl-propan-1-ol and S-(carboxymethyl)-(R)-cysteine; the salt of (1S,2R)-2-amino-1-phenyl-propan-1-ol and S-(carboxymethyl)-(S)-cysteine is considerably less soluble than the diastereomer salt thereto from (1R,2S-2-amino-1-phenyl-propan-1-ol and S-(carboxymethyl)-(S)-cysteine.

To carry out the process of the invention, the procedure is as customary in the separation of a racemate. The racemate (1RS,2SR)-2-amino-1-phenyl-propan-1-ol in the presence of a solvent is brought together with the desired optical isomer of S-(carboxymethyl)-cysteine and then the diastereomer salts formed are resolved.

The salts which are diastereomers to each other in numerous solvents show sufficiently large differences in solubility. For example, water is included in these solvents. Preferably, there are used as solvents primary or secondary alkanols having up to 6 carbon atoms or ethers and among these solvents especially those which are unlimitedly miscible with water. For example, there can be used hexan-1-ol, butan-1-ol, methyl tert. butyl ether, and especially methanol, ethanol, propan-2-ol, dioxane, and tetrahydrofurane. Other solvents include propan-1-ol, butan-2-ol, 2-methyl-propan-1-ol. The solvents can also be used in mixtures with each other or in mixtures with water, but the mixtures are suitably so selected that the solvents form a single phase.

The racemate (1RS,2SR)-2-amino-1-phenyl-propan-1-ol, as well as the optical isomer concerned of the S-(carboxymethyl)-cysteine can be employed in solid form or as a suspension or solution in the solvent. The optical isomer of S-(carboxymethyl)-cysteine and the racemate (1RS,2SR)-2-amino-1-phenyl-propan-1-ol can be employed in any desired proportion to each other. However, generally it is suitable to employ per mole of the racemate not less than about 0.5 and not more than about 5.0 moles of the optical isomer. Preferably, per mole of the racemate there is used 0.9 to 1.1, especially 1.0, mole of the optical isomer. There can be employed all temperatures at which the solvent is present in liquid form.

For resolution of the diastereomer salts, the preferred procedure is by a fractional crystallization in the customary manner. The mixture is brought to elevated temperatures, preferably to temperatures near the boiling point, so much solvent used that all materials are dissolved, and subsequently the solution cooled for the crystallization.

The concerned 2-amino-1-phenyl-propan-1-ol is set free from the precipitated salts from (1R,2S)-2-amino-1-phenyl-propan-1-ol and S-(carboxymethyl)-(R)-cysteine or (1S,2R)-2-amino-1-phenyl-propan-1-ol and S-(carboxymethyl)-(S)-cysteine by treating the salts with strong acids, preferably strong mineral acids such as hydrochloric acid. Other mineral acids include hydrobromic acid and sulfuric acid.

Unless otherwise indicated, all parts and percentages are by weight.

The compositions can comprise, consist essentially of, or consist of the stated materials; and the process can comprise, consist essentially of, or consist of the steps set forth with the stated materials.

DETAILED DESCRIPTION

EXAMPLES

The optically active materials obtained in each case were examined as to their specific rotation $[\alpha]_D^T$. This is given in degrees·cm$^3$/dm.g. Percent data are weight percents.

EXAMPLE 1

A mixture of 50 grams (0.28 mole) of S-(carboxymethyl)-(R)-cysteine and 42.5 grams (0.28 mole) of (1RS,2SR)-2-amino-1-phenyl-propan-1-ol were dissolved in 50 ml of water. The solution was held at 30° to 40° C. and treated dropwise with ethanol until crystalization began, then cooled slowly to 5° C. and filtered under suction. The residue was washed with 150 ml of ethanol which contained 10% of water and dried at 50° C. and 25 mbar. The material recovered was the salt of S-(carboxymethyl)-(R)-cysteine and (1R,2S)-2-amino-1-phenyl-propan-1-ol. The yield was 44.8 grams, corresponding to 97% based on the (1R,2S)-2-amino-1-phenyl-propan-1-ol contained in the racemate employed. The melting point of the salt recovered was 66° C. and the specific rotation −37.2° (T=20° C.; c=1 in water).

The salt was dissolved in 150 ml of water and the solution adjusted to pH 2.8 by means of 2 N aqueous sulfuric acid at 25° C. Hereby, the S-(carboxymethyl)-(R)-cysteine was precipitated. It was filtered off. The filtrate was treated with 200 ml of a 50% aqueous sodium hydroxide solution. The mixture was extracted three times, each time with 100 ml of methylene chloride. The combined extracts were dried with sodium sulfate. Then the methylene chloride was driven off and the residue recrystallized in methyl tert. butyl ether. There were obtained 19.6 grams of (1R,2S)-2-amino-1-phenyl-propan-1-ol, corresponding to a yield of 95% based on the (1R,2S)-2-amino-1-phenyl-propan-1-ol contained in the racemate employed. The specific rotation of the material recovered was −13.9° (T=20° C.; c=1 in water free ethanol).

The filtrate remaining after filtering off the salt of S-(carboxymethyl)-(R)-cysteine and (1R,2S)-2-amino-1-phenyl-propan-1-ol was adjusted to pH 3.0 with 2 N aqueous hydrochloric acid. Hereby, there was precipitated S-(carboxymethyl)-(R)-cysteine. The material was filtered off, combined with the S-(carboxymethyl)-(R)-cysteine previously set free from its salt, then washed with 50 ml of 0.001 N aqueous hydrochloric acid and dried at 105° C. There were recovered 47.5 grams, corresponding to 95%, of the S-(carboxymethyl)-(R)-cysteine employed. The material could be used directly for further resolution.

The last filtrate remaining after filtering off the S-(carboxymethyl)-(R)-cysteine was treated with 200 ml of 50% aqueous sodium hydroxide solution. The mixture was extracted three times, each time with 100 ml of methylene chloride. The combined extracts were dried with sodium sulfate. Then the methylene chloride was driven off and the residue recrystallized in di-isopropyl ether. There were obtained hereby 14.5 grams of (1S,2R)-2-amino-1-phenyl-propan-1-ol corresponding to 71% of the (1S,2R)-2-amino-1-phenyl-propan-1-ol in the racemate employed. The specific rotation of the substance obtained was +14.4° (T=27° C.; c=4 in water free ethanol).

EXAMPLE 2

50 grams (0.28 mole) of S-(carboxymethyl)-(R)-cysteine were suspended in 400 ml of ethanol which contained 10% of water. To this suspension there were added 42.5 grams (0.28 mole) of (1RS,2SR)-2-amino-1-phenyl-propan-1-ol. The mixture was held at that time at 40° to 50° C. and then for one hour under reflux at the boiling point, then cooled to 23° C. in the course of 30 minutes and filtered under suction. The residue was washed with 200 ml of methanol and dried at 50° C. and 25 mbar. There were obtained 41.6 grams of the salt of S-(carboxymethyl)-(R)-cysteine and (1R,2S)-2-amino-1-phenyl-propan-1-ol*) The melting point was 68° C. and the specific rotation −38.2° (T=20° C.; c=1 in water).
*) corresponding to a yield of 90% based on the (1R,2S)-2-amino-1-phenyl-propan-1-ol in the racemate added.

The salt was dissolved in 150 ml of water at 25° C. and the solution adjusted to pH 3.0 with 2 N aqueous hydrochloric acid. Hereby, the S-(carboxymethyl)-(R)-cysteine precipitated. It was filtered off with suction. There were obtained 20.3 grams, corresponding to 90% based on the S-(carboxymethyl)-(R)-cysteine employed. The filtrate was evaporated to dryness. There were obtained 21.9 grams of (1R,2S)-2-amino-1-phenyl-propan-1-ol-hydrochloride, corresponding to a yield of 98% based on the (1R,2S)-2-amino-1-phenyl-propan-1-ol in the racemate added.**) The melting point then was 165° C. and the specific rotation −36.0° (T=20° C.; c=1 in water).
**) The material obtained was recrystallized in propan-2-ol.

EXAMPLE 3

The procedure was as in Example 2, but the S-(carboxymethyl)-(R)-cysteine was added in 1000 ml of water free methanol. There were obtained 37.0 grams, corresponding to an 80% yield of the salt of S-(carboxymethyl)-(R)-cysteine and (1R,2S)-2-amino-1-phenyl-propan-1-ol. The melting point of the salt was 67° C. and the rotation −37.5° (T=20° C.; c=1 in water). The elemental analysis of the salt showed:
C=50.65% (50.89%); H=6.70% (6.71%);
N=8.50% (8.48%); S=9.79% (9.71%). (Calculated for $C_{14}H_{22}N_2O_5S$).

EXAMPLE 4

The procedure was as in Example 1, but the starting materials were suspended in 800 ml of dioxane and there was supplied water to this suspension at the boiling point until all materials were dissolved. The solution was cooled in the course of 2 hours to 18° C. There were obtained 36.1 grams, corresponding to 78% yield of the salt of S-(carboxymethyl)-(R)-cysteine and (1R,2S)-2-amino-1-phenyl-propan-1-ol. The melting point was 68° C. and the rotation −37.4° (T=20° C.; c=1 in water).

EXAMPLE 5

The procedure was as in Example 4; but in place of the dioxane, there were employed 800 ml of propan-2-ol as solvent. There were obtained 43.9° grams of the salt of S-(carboxymethyl)-(R)-cysteine and (1R,2S)-2-amino-1-phenyl-propan-1-ol, corresponding to a yield of 95%. The melting point was 68° C. and the rotation −38.1° (T=20° C.; c=1 in water).

EXAMPLE 6

The procedure was as in Example 4; but instead of the dioxane, there were employed 200 ml of tetrahydrofurane as solvent. There were obtained 44.4 grams of the salt of S-(carboxymethyl)-(R)-cysteine and (1R,2S)-2-amino-1-phenyl-propan-1-ol, corresponding to a yield of 96%. The melting point was 60° C. and the rotation −38.8° (T=20° C.; c=1 in water).

EXAMPLE 7

The procedure was as in Example 1, but there was employed a mixture of 100 grams (0.56 mole) of S-(carboxymethyl)-(R)-cysteine and 124 grams (0.82 mole) of (1RS,2SR)-2-amino-1-phenyl-propan-1-ol in 800 ml of methanol which contained 2% of water. The mixture was held for one hour under reflux at the boiling point and then cooled to 30° C. in the course of 30 minutes. There were obtained 89.6 grams, corresponding to 97%, of the salt of S-(carboxymethyl)-(R)-cysteine and (1R,2S)-2-amino-1-phenyl-propan-1-ol. The melting point of the salt was 67° C. and the rotation −37.3° C. (T=20° C.; c=1 in water).

EXAMPLE 8

The procedure was as in Example 1, except that in place of S-(carboxymethyl)-(R)-cysteine there were employed 50.0 grams (0.28 mole) of S-(carboxymethyl)-(S)-cysteine. There were obtained the salt of S-(carboxymethyl)-(S)-cysteine and (1S,2R)-2-amino-1-phenyl-propan-1-ol. The yield was 44.0 grams, corresponding to 95% based on the (1S,2R)-2-amino-1-phenyl-propan-1-ol contained in the racemate. The specific rotation of the salt obtained was +37.3° (T=20° C.; c=1 in water). The elemental analysis showed:

C=50.70% (50.89%); H=6.65% (6.71%);
N=8.59% (8.48%); S=9.59% (9.71%).
(Calculated for $C_{14}H_{22}N_2O_5S$).

The salt was dissolved in 100 ml of water and the solution adjusted to pH 3.0 with 2 N aqueous hydrochloric acid. Hereby, the S-(carboxymethyl)-(S)-cysteine was precipitated. It was filtered off. The filtrate was evaporated to dryness. The residue was recrystallized in propan-2-ol. There were obtained 24.0 grams of (1S,2R)-2-amino-1-phenyl-propan-1-ol hydrochloride, corresponding to 96% yield based on the (1S,2R)-2-amino-1-phenyl-propan-1-ol contained in the racemate employed. The melting point was 174° to 176° C. and the specific rotation +33.4° (T=23° C.; c=7 in water).

The filtrate remaining after filtering off the salt of S-(carboxymethyl)-(S)-cysteine and (1S,2R)-2-amino-1-phenyl-propan-1-ol was evaporated to dryness. Hereby, there were obtained 44 grams of the salt of S-(carboxymethyl)-(S)-cysteine and (1R,2S)-2-amino-1-phenyl-propan-1-ol, corresponding to a yield of 95% based on the (1R,2S)-2-amino-1-phenyl-propan-1 contained in the racemate employed.

The salt was dissolved in 100 ml of water and the solution adjusted to pH 3.0 by means of 2 N aqueous hydrochloric acid. Hereby, the S-(carboxymethyl)-(S)-cysteine precipitated. It was filtered off. The filtrate was evaporated to dryness. The residue was recrystallized in propan-2-ol. There were obtained 18.7 grams of (1R,2S)-2-amino-1-phenyl-propan-1-ol hydrochloride, corresponding to a yield of 71% based on the (1R,2S)-2-amino-1-phenyl-propan-1-ol in the racemate employed. The specific rotation was −31.1° (T=20° C.; c=1 in water).

The entire disclosure of German priority application Ser. No. P 3134129.2 is hereby incorporated by reference.

What is claimed is:

1. A process of resolving the racemate (1RS,2SR)-2-amino-1-phenyl-propan-1-ol comprising dissolving the racemate together with an optical isomer of S-(carboxymethyl)-cysteine in a solvent in which the salt of said optical isomer with one of the isomers present in said racement is less soluble than the salt of said optical isomer with the other one of the isomers present in said racemate and precipitating the less soluble salt.

2. A process according to claim 1 wherein the solvent is water, a primary or secondary alkanol having 1 to 6 carbon atoms, an ether or a mixture of such solvents.

3. A process according to claim 2 wherein the solvent is methanol, ethanol, propan-2-ol, dioxane, or tetrahydrofuran or a mixture of such solvent with a minor amount of water.

4. A process according to claim 3 wherein the solvent is anhydrous.

5. A process according to claim 3 wherein the solvent contains a minor amount of water.

6. A process according to claim 2 wherein the solvent comprises an alkanol having 1 to 6 carbon atoms.

7. A process according to claim 2 wherein the solvent comprises di-isopropyl ether, methyl tert. butyl ether, dioxane, or tetrahydrofurane.

8. A process according to claim 3 wherein the solvent comprises methanol, ethanol, or propan-2-ol.

9. A compound which is either (1) a salt of S-(carboxymethyl)-(R)-cysteine and (1R,2S)-2-amino-1-phenyl-propan-1-ol or (2) a salt of S-(carboxymethyl)-(S)-cysteine and (1S,2R)-2-amino-1-phenyl-propan-1-ol.

10. A compound according to claim 9 which is a salt of S-(carboxymethyl)-(R)-cysteine and (1R,2S)-2-amino-1-phenyl-propan-1-ol.

11. A composition comprising the compound of claim 10 substantially free from the salt of S-(carboxymethyl)-(R)-cysteine and (1S,2R)-2-amino-1-phenyl-propan-1-ol.

12. A compound according to claim 9 which is a salt of S-(carboxymethyl)-(S)-cysteine and (1S,2R)-2-amino-1-phenyl-propan-1-ol.

13. A composition comprising the compound of claim 12 substantially free from the salt of S-(carboxymethyl)-(S)-cysteine and (1R,2S)-2-amino-1-phenyl-propan-1-ol.

* * * * *